(12) United States Patent
Fadli

(10) Patent No.: US 8,568,491 B2
(45) Date of Patent: Oct. 29, 2013

(54) CATIONIC 4-AMINOINDOLES, DYE COMPOSITION COMPRISING A CATIONIC 4-AMINOINDOLE, PROCESSES THEREFOR AND USES THEREOF

(75) Inventor: Aziz Fadli, Chelles (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/514,589

(22) PCT Filed: Dec. 6, 2010

(86) PCT No.: PCT/EP2010/068947
§ 371 (c)(1),
(2), (4) Date: Oct. 18, 2012

(87) PCT Pub. No.: WO2011/069952
PCT Pub. Date: Jun. 16, 2011

(65) Prior Publication Data
US 2013/0025618 A1 Jan. 31, 2013

Related U.S. Application Data

(60) Provisional application No. 61/287,385, filed on Dec. 17, 2009.

(30) Foreign Application Priority Data

Dec. 7, 2009 (FR) ...................... 09 58717

(51) Int. Cl.
*A61Q 5/10* (2006.01)
*C07D 209/04* (2006.01)

(52) U.S. Cl.
USPC ............. 8/409; 8/423; 8/426; 8/574; 548/490

(58) Field of Classification Search
USPC ....................... 8/409, 423, 426, 574; 548/490
See application file for complete search history.

(56) References Cited

U.S. PATENT DOCUMENTS 6,306,181 B1 * 10/2001 Terranova et al. ................ 8/409

OTHER PUBLICATIONS

STIC Search Report dated Nov. 29, 2012.*

* cited by examiner

*Primary Examiner* — Eisa Elhilo
(74) *Attorney, Agent, or Firm* — John A. Artz; Dickinson Wright PLLC

(57) ABSTRACT

The present invention relates to a cationic 4-aminoindole of general formula (I), addition salts thereof with an acid and solvates thereof: in which: $R_1$ is a linear or branched, saturated $C_2$-$C_{20}$ alkyl radical, substituted and/or interrupted with a cationic radical. The present invention is also directed towards a process for synthesizing this cationic 4-aminoindole, to the compositions, the uses, the hair dyeing processes and the devices using this cationic 4-aminoindole.

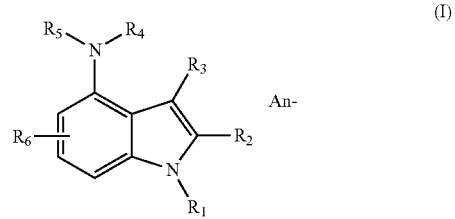

14 Claims, No Drawings

CATIONIC 4-AMINOINDOLES, DYE COMPOSITION COMPRISING A CATIONIC 4-AMINOINDOLE, PROCESSES THEREFOR AND USES THEREOF

This application is a national phase application based on PCT/EP2010/068947 filed Dec. 6, 2010, which claims priority from French Application No. 0958717, filed Dec. 7, 2009, and claims the benefit of U.S. Provisional Application No. 61/287,385, filed on Dec. 17, 2009, the content of all of which is incorporated herein by reference in their entirety.

TECHNICAL FIELD

The present invention relates to novel cationic 4-aminoindoles, to their use for dyeing keratin fibres, in particular human keratin fibres such as the hair, to dye compositions comprising such cationic 4-aminoindoles, and to processes and devices using these cationic 4-aminoindoles.

BACKGROUND

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases can be varied by combining them with couplers or coloration modifiers, the latter being chosen especially from aromatic meta-diaminobenzenes, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired intensity and it must show good remanance with respect to external agents such as light, bad weather, washing, permanent-waving, perspiration and rubbing.

The dyes must also allow grey hair to be covered, and they must be as unselective as possible, i.e. they must produce the smallest possible coloration differences along the same length of a keratin fibre, which is generally differently sensitized (i.e. damaged) between its end and its root.

SUMMARY OF THE INVENTION

The Applicant has discovered, surprisingly and advantageously, a novel family of heterocyclic couplers formed from cationic 4-aminoindoles. These couplers can produce novel compositions for dyeing keratin fibres, which are capable of giving colorations in varied, powerful, chromatic shades.

These compositions are also sparingly selective and are fast: they show good resistance to the various attacking factors to which the fibres may be subjected.

Moreover, these heterocyclic couplers show good solubility, allowing satisfactory uptake of the colour.

A first subject of the invention concerns a family of cationic 4-aminoindoles and processes for synthesizing them.

A subject of the invention is also a composition containing at least one cationic 4-aminoindole, dyeing processes using this composition, the uses of the said composition according to the present invention for dyeing keratin fibres, in particular human keratin fibres such as the hair, and in particular multi-compartment devices or dyeing "kits".

Other characteristics, aspects, subjects and advantages of the present invention will emerge even more clearly on reading the description and the examples that follow.

DESCRIPTION OF THE PREFERRED EMBODIMENTS

The present invention relates to a cationic 4-aminoindole of general formula (I), the addition salts thereof with an acid and the solvates thereof:

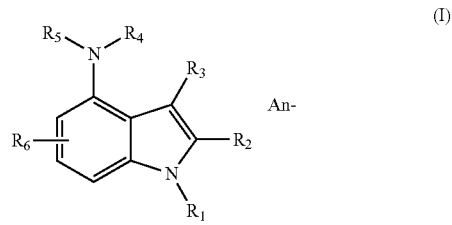

in which:

$R_1$ is a linear or branched saturated $C_2$-$C_{20}$ alkyl radical, which is substituted or interrupted with a cationic radical, $R_1$ also optionally being interrupted with one or more oxygen atoms and/or with one or more groups $NR_7$;

$R_7$ is a hydrogen atom or a linear or branched $C_1$-$C_4$ alkyl radical, a benzyl radical or an acetyl radical;

$R_2$, $R_3$ and $R_6$, independently of each other, are chosen from: a hydrogen atom, halogens chosen from fluorine, chlorine and bromine, and linear or branched $C_1$-$C_4$ alkyl, carboxyl (—COOH) or ($C_1$-$C_4$)alkoxycarbonyl radicals;

$R_4$ and $R_5$, independently of each other, are chosen from: a hydrogen atom and $C_1$-$C_4$ alkyl radicals;

An- represents an anion or a mixture of anions.

In the context of the invention, the term "cationic radical" present in the compound of formula (I) means any linear, branched or cyclic, saturated or unsaturated radical, comprising a quaternary ammonium in the radical or substituent radical, this quaternary ammonium being of the type —N⁺RaRb- or —N⁺RaRbRc, with Ra, Rb and Rc, which may be identical or different, representing a $C_1$-$C_6$ alkyl radical that may be substituted with a hydroxyl. Ra and Rb may together form a saturated or unsaturated 5- to 8-membered heterocycle, Rc, when it is present, then being a $C_1$-$C_6$ alkyl radical that may be substituted with a hydroxyl.

When the cationic radical present in the compound of formula (I) comprises a quaternary ammonium of the type —N⁺RaRbRc, and when Ra and Rb form, together with the nitrogen atom to which they are attached, an unsaturated heterocycle such as a pyridinium, then the quaternary ammonium does not bear a group Rc.

Examples of quaternary ammoniums of the type —N⁺RaRbRc that may be mentioned include trimethylammonium, triethylammonium, dimethylethylammonium, diethylmethylammonium, diisopropylmethylammonium, diethylpropylammonium, hydroxyethyldiethylammonium, di-β-hydroxyethylmethylammonium, tri-β-hydroxyethylammonium, N-methylpiperidinium, N-methylpyrrolidinium, N-methylmorpholinium, N-methylimidazolium, 1-methylpiperazin-1-ium, pyridinium, pyrimidinium, thiazolium, benzimidazolium, benzothiazolium, oxazolium, benzotriazolium, pyrazolium, triazolium and benzoxazolium.

As examples of cyclic radicals other than the one formed by —N⁺RaRbRc as defined previously, mention may be made of pyrrolidine, morpholine and piperidine.

For the purposes of the present patent application, the term "cationic heterocycle" means a 5- to 8-membered heterocycle, at least one of the ring members of which is a quaternary ammonium. Examples of cationic heterocyclic radicals that may be mentioned include imidazolium, pyridinium, piperazinium, piperidinium, pyrrolidinium, morpholinium, pyrimidinium, thiazolium, benzimidazolium, benzothiazolium, oxazolium, benzotriazolium, pyrazolium, triazolium and benzoxazolium radicals.

Preferably, $R_1$ is a linear or branched, saturated $C_2$-$C_{20}$ alkyl radical, substituted or interrupted with a cationic radical as defined previously, not interrupted or interrupted with one or more oxygen atoms and/or with one or more groups $NR_7$. Preferably, $R_7$ is a hydrogen atom.

Even more preferably, $R_1$ is a linear or branched, saturated $C_2$-$C_{10}$ alkyl radical, substituted or interrupted with a cationic radical as defined previously, not interrupted or interrupted with one or more oxygen atoms and/or with one or more NH groups.

Preferably, the cationic radicals are chosen from trimethylammonium, triethylammonium, dimethylethylammonium, diethylmethylammonium, diisopropylmethylammonium, diethylpropylammonium, hydroxyethyldiethylammonium, di-β-hydroxyethylmethylammonium, tri-β-hydroxyethylammonium, imidazolium, N-methylimidazolium, pyridinium, 1-methylpiperazin-1-ium, N,N-dimethylpiperazinium, N-methylpiperidinium, N-methylpyrrolidinium, N-methylmorpholinium, pyrimidinium, thiazolium, benzimidazolium, pyrrolidine substituted with a trimethylammonium group, piperidine substituted with a trimethylammonium group, morpholine substituted with a trimethylammonium group, trimethylethanammonium, methyldiethylmethanammonium, methyldiethylethanammonium, methylmethanopyrrolidinium and methylethanopyrrolidinium radicals.

Even more preferably, the cationic radicals are chosen from trimethylammonium, imidazolium, N,N-dimethylpiperazinium, pyrrolidine substituted with a trimethylammonium group, piperidine substituted with a trimethylammonium group, morpholine substituted with a trimethylammonium group, trimethylethanammonium, methyldiethylmethanammonium, methyldiethylethanammonium, methylmethanopyrrolidinium and methylethanopyrrolidinium radicals.

According to one particularly preferred variant of the invention, $R_1$ represents a linear saturated $C_2$-$C_8$ alkyl radical, which is not interrupted or interrupted with an oxygen atom or an NH group, substituted with a cationic radical chosen from the radicals: trimethylammonium, imidazolium, N-methylimidazolium, N-methylpiperidinium, N,N-dimethylpiperazinium, 1-methylpiperazin-1-ium, N-methylpyrrolidinium, N-methylmorpholinium, pyrrolidine substituted with a trimethylammonium group, piperidine substituted with a trimethylammonium group, morpholine substituted with a group selected from trimethylammonium, methyldiethylmethanammonium, trimethylethanammonium, methylpyrrolidinium, methyldiethylethanammonium, methylethanopyrrolidinium and methylmethanopyrrolidinium.

Preferably, $R_2$, $R_3$ and $R_6$, independently of each other, are chosen from a hydrogen atom and $C_1$-$C_4$ alkyl radicals. Even more preferably, $R_2$, $R_3$ and $R_6$ are hydrogen atoms.

Preferably, $R_4$ and $R_5$ are identical and represent hydrogen atoms.

The cationic 4-aminoindoles of general formula (I) may be present in free form or in the form of salts, such as addition salts with a mineral acid preferably chosen from hydrochlorides, hydrobromides, sulfates, or phosphates, or with an organic acid, for instance citrates, succinates, tartrates, lactates, tosylates, benzenesulfonates, acetates, para-toluenesulfonates, formates or methanesulfonates.

The cationic 4-aminoindoles of general formula (I) may also be in the form of solvates, for example a hydrate or a solvate of a linear or branched alcohol such as ethanol or isopropanol.

In the context of the invention, the term "derivative of formula (I)" means any mesomeric or isomeric form.

The electrical neutrality of the compounds of formula (I) is ensured by one or a mixture of cosmetically acceptable organic or mineral anions, noted An-.

An- represents an anion or a mixture of anions chosen, for example, from a halide, such as chloride, bromide, fluoride or iodide; a hydroxide; a sulfate; a hydrogen sulfate; an alkyl sulfate for which the linear or branched alkyl part is $C_1$-$C_6$, for instance the methyl sulfate or ethyl sulfate ion; carbonates and hydrogen carbonates; carboxylic acid salts such as formate, acetate, citrate, tartrate or oxalate; alkylsulfonates for which the linear or branched alkyl part is of $C_1$-$C_6$, for instance the methylsulfonate ion; arylsulfonates for which the aryl part, preferably phenyl, is optionally substituted with one or more $C_1$-$C_4$ alkyl radicals, for instance 4-tolylsulfonate; alkylsulfonyls such as mesylate.

Preferably, the cationic 4-aminoindoles of general formula (I) are chosen from the following compounds:

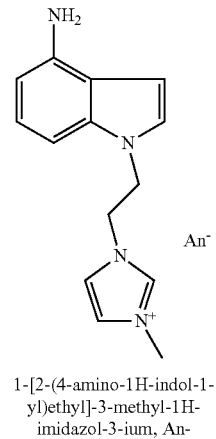

(Compound 1)

1-[2-(4-amino-1H-indol-1-yl)ethyl]-3-methyl-1H-imidazol-3-ium, An-

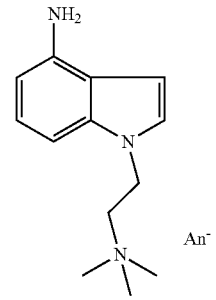

(Compound 2)

2-(4-amino-1H-indol-1-yl)-N,N,N-trimethylethanammonium, An- (Compound 3)

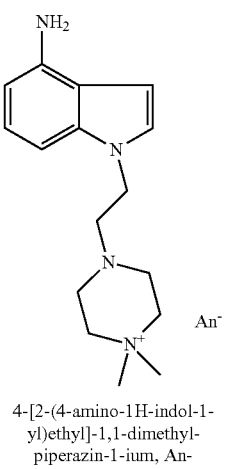

4-[2-(4-amino-1H-indol-1-yl)ethyl]-1,1-dimethyl-piperazin-1-ium, An- (Compound 4)

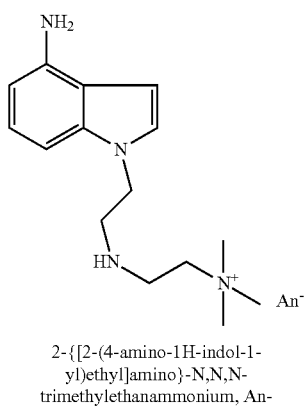

2-{[2-(4-amino-1H-indol-1-yl)ethyl]amino}-N,N,N-trimethylethanammonium, An- (Compound 5)

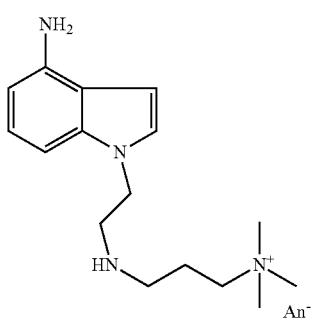

3-{[2-(4-amino-1H-indol-1-yl)ethyl]amino}-N,N,N-trimethylpropan-1-ammonium, An- (Compound 6)

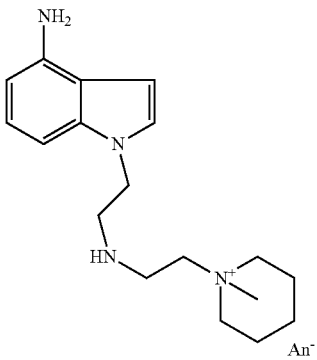

1-(2-{[2-(4-amino-1H-indol-1-yl)ethyl]amino}ethyl)-1-methylpiperidinium, An- (Compound 7)

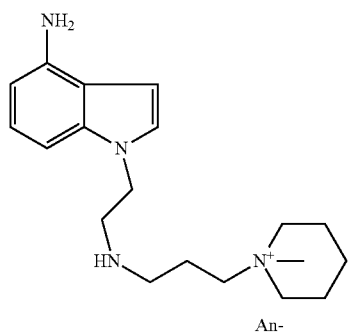

1-(3-{[2-(4-amino-1H-indol-1-yl)ethyl]amino}propyl)-1-methyl piperidinium, An- (Compound 8)

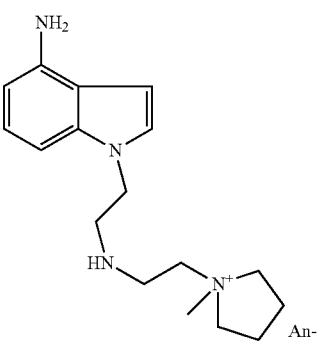

1-(2-{[2-(4-amino-1H-indol-1-yl)ethyl]amino}ethyl)-1-methylpyrrolidinium, An- (Compound 9)

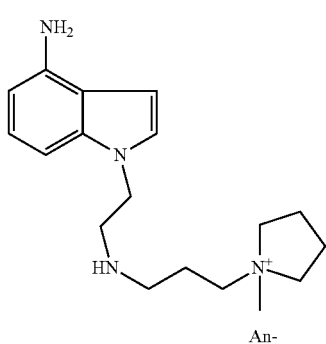

1-(2-{[2-(4-amino-1H-indol-
1-yl)ethyl]amino}ethyl)-1-
methylpyrrolidinium, An- (Compound 10)

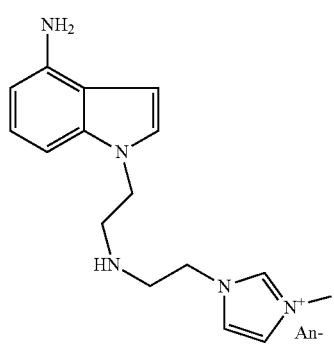

1-(2-{[2-(4-amino-1H-indol-
1-yl)ethyl]amino}ethyl)-3-
methyl-1H-imidazol-3-ium, An- (Compound 11)

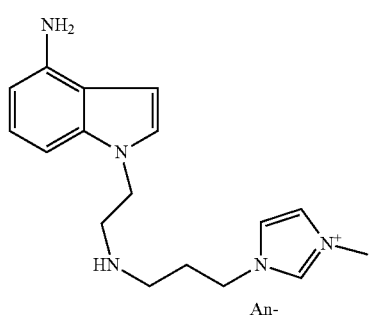

1-(3-{[2-(4-amino-1H-indol-
1-yl)ethyl]amino}propyl)-3-
methyl-1H-imidazol-3-ium, An- (Compound 12)

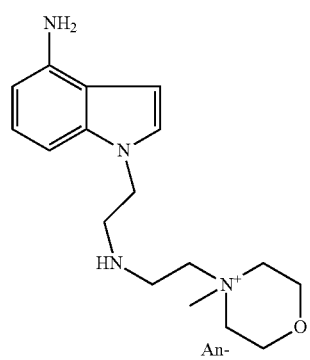

4-(2-{[2-(4-amino-1H-indol-
1-yl)ethyl]amino}ethyl)-4-
methylmorpholin-4-ium, An- (Compound 13)

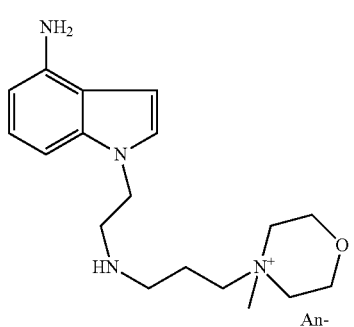

4-(3-{[2-(4-amino-1H-indol-
1-yl)ethyl]amino}propyl)-4-
methylmorpholin-4-ium, An- (Compound 14)

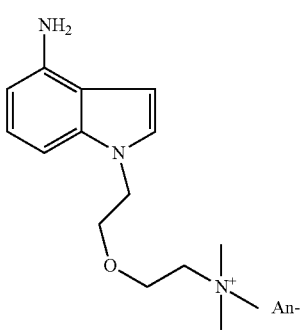

2-[2-(4-amino-1H-indol-1-
yl)ethoxy]-N,N,N-trimethyl-
ethanammonium, An- (Compound 15)

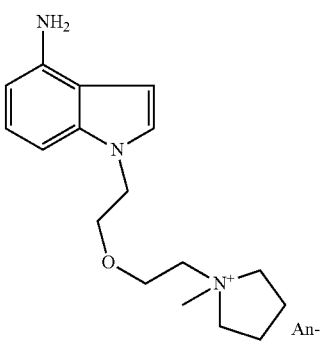

1-{2-[2-(4-amino-1H-indol-1-
yl)ethoxy]ethyl}-1-methyl-
pyrrolidinium, An- (Compound 16)

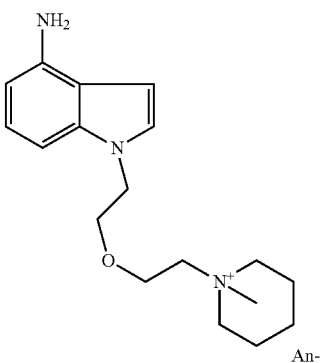

1-{2-[2-(4-amino-1H-indol-1-
yl)ethoxy]ethyl}-1-methyl-
piperidinium, An-

-continued (Compound 17)

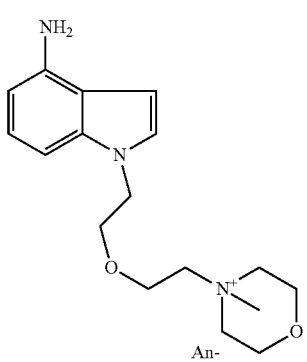

4-{2-[2-(4-amino-1H-indol-1-yl)ethoxy]ethyl}-4-methyl-morpholin-4-ium, An- (Compound 18)

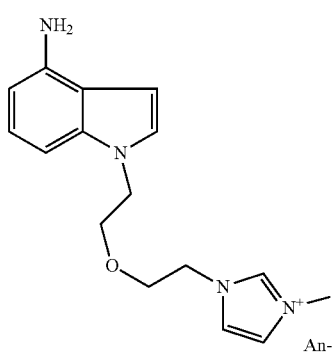

1-{2-[2-(4-amino-1H-indol-1-yl)ethoxy]ethyl}-3-methyl-1H-imidazol-3-ium, An- (Compound 19)

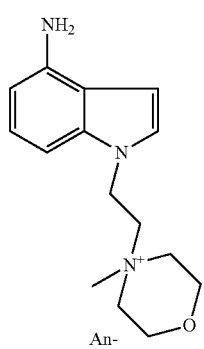

4-[2-(4-amino-1H-indol-1-yl)ethyl]-4-methylmorpholin-4-ium, An- (Compound 20)

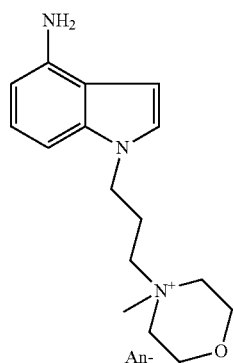

4-[3-(6-amino-2,3-dihydro-1H-indol-1-yl)propyl]-4-methylmorpholin-4-ium, An- (Compound 21)

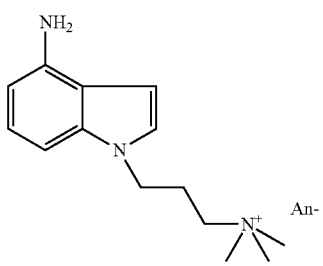

3-(4-amino-1H-indol-1-yl)-N,N,N-trimethylpropan-1-ammonium, An- (Compound 22)

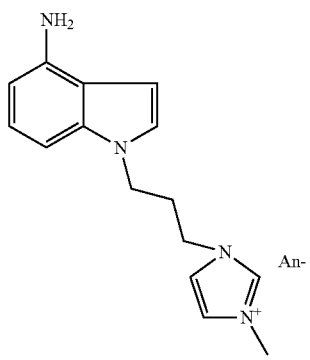

1-[3-(4-amino-1H-indol-1-yl)propyl]-3-methyl-1H-imidazol-3-iu, An- (Compound 23)

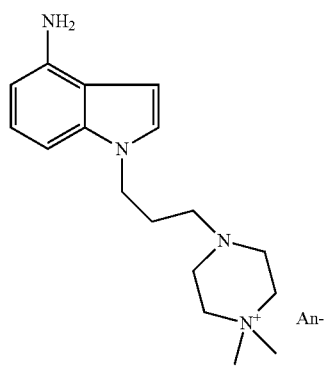

4-[3-(4-amino-1H-indol-1-yl)propyl]-1,1-dimethyl-piperazin-1-ium, An- (Compound 24)

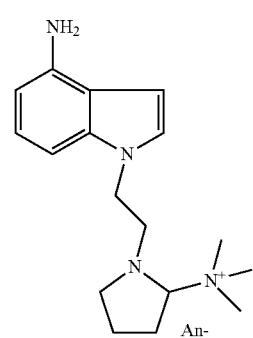

1-[2-(4-amino-1H-indol-1-yl)ethyl]-N,N,N-trimethyl-pyrrolidin-2-ammonium, An- (Compound 25)

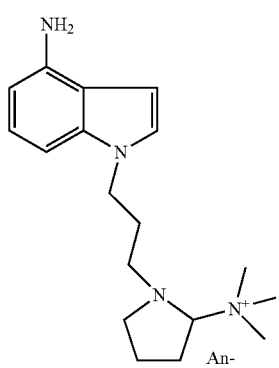

1-[3-(4-amino-1H-indol-1-yl)propyl]-N,N,N-trimethyl-pyrrolidin-2-ammonium, An- (Compound 26)

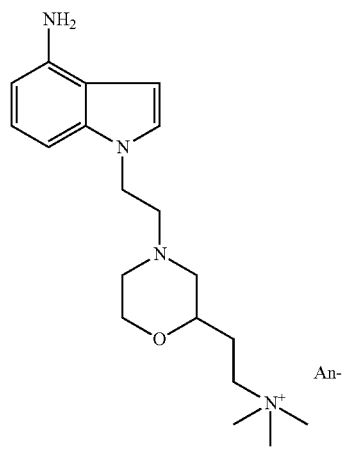

4{2-[3-(4-amino-1H-indol-1-yl)]ethyl}-N,N,N-trimethyl-morpholin-2-ethanammonium, An- (Compound 26 bis)

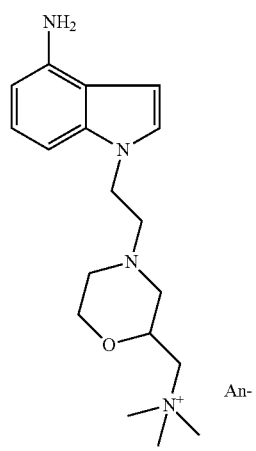

4{2-[3-(4-amino-1H-indol-1-yl)]ethyl}-N,N,N-trimethyl-morpholin-2-methanammonium, An- (Compound 27)

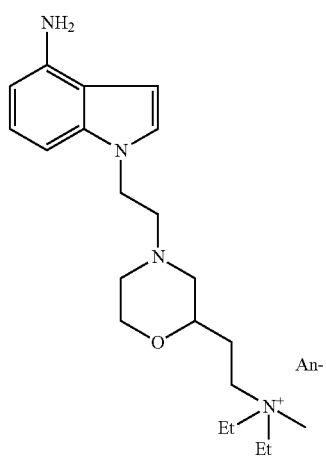

4{2-[3-(4-amino-1H-indol-1-yl)]ethyl}-N,N,N-diethyl-methylmorpholin-2-ethanammonium, An- -continued

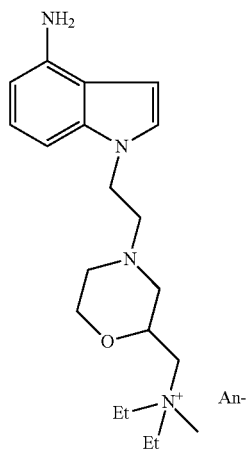

(Compound 27 bis)

4{2-[3-(4-amino-1H-indol-1-yl)]ethyl}-N,N-diethylmorpholin-2-methanammonium, An-

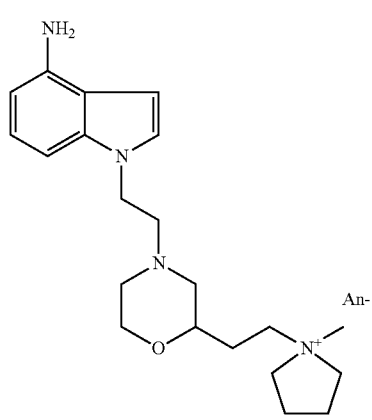

(Compound 28)

4{2-[3-(4-amino-1H-indol-1-yl)]ethyl}-N,N,N-morpholin-2-ethan-1-methyl-pyrrolidinium, An-

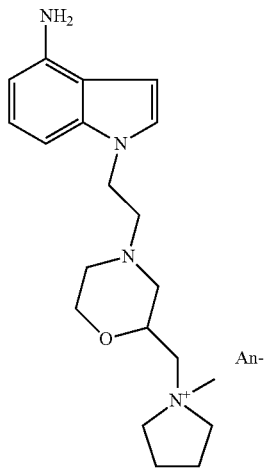

(Compound 28 bis)

4{2-[3-(4-amino-1H-indol-1-yl)]ethyl}-N,N,N-morpholin-2-methan-1-methyl-pyrrolidinium, An-

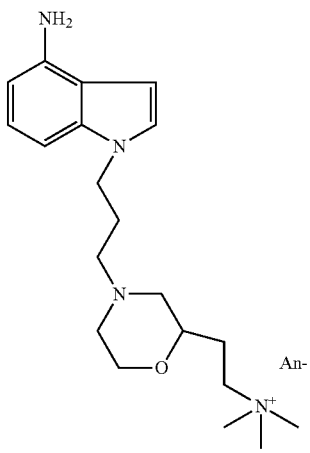

(Compound 29)

4{3-[3-(4-amino-1H-indol-1-yl)]propyl}-N,N,N-trimethyl morpholin-2-ethanammonium, An-

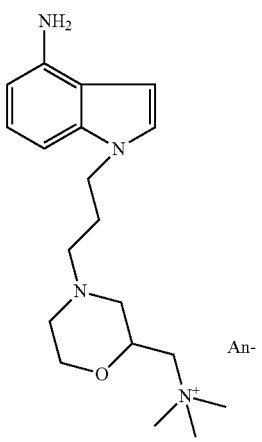

(Compound 29 bis)

4{3-[3-(4-amino-1H-indol-1-yl)]propyl}-N,N,N-trimethyl-morpholin-2-methanammonium, An-

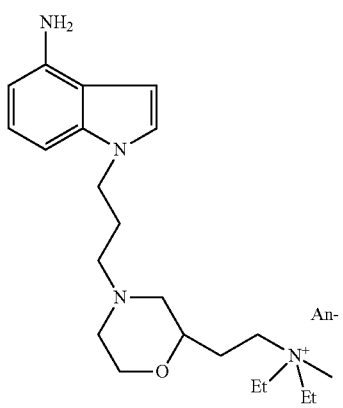

(Compound 30)

4{3-[3-(4-amino-1H-indol-1-yl)]propyl}-N,N,N-diethylmethylmorpholin-2-ethanammonium, An- (Compound 30 bis)

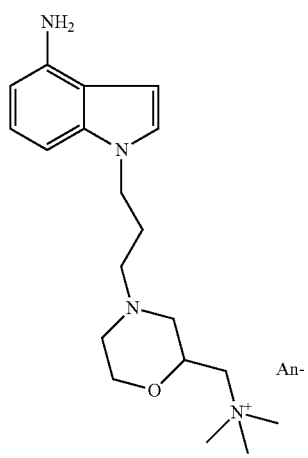

4{3-[3-(4-amino-1H-indol-1-yl)]propyl}-N,N,N-diethylmethylmorpholin-2-methanammonium, An- (Compound 31)

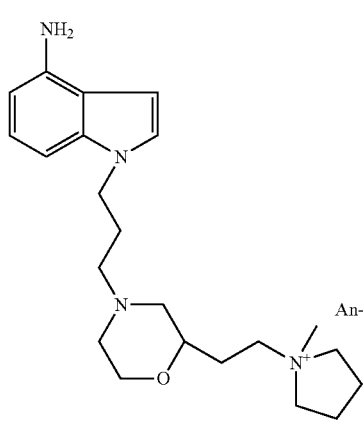

4{3-[3-(4-amino-1H-indol-1-yl)]propyl}-N,N,N-morpholin-2-ethan-1-methylpyrrolidinium, An- (Compound 31 bis)

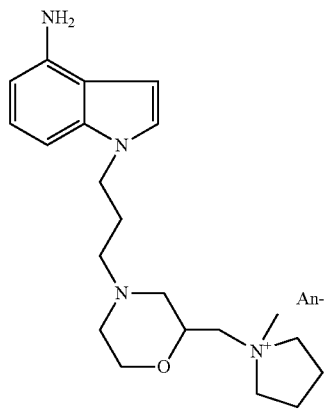

4{3-[3-(4-amino-1H-indol-1-yl)]propyl}-N,N,N-morpholin-2-methan-1-methylpyrrolidinium, An- (Compound 32)

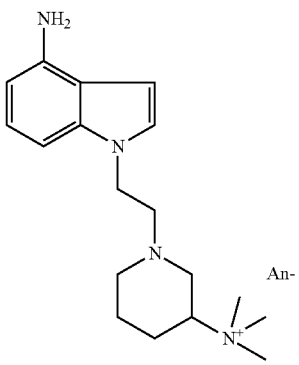

1-[2-(4-amino-1H-indol-1-yl)ethyl]-N,N,N-trimethyl piperidin-3-ammonium, An- (Compound 33)

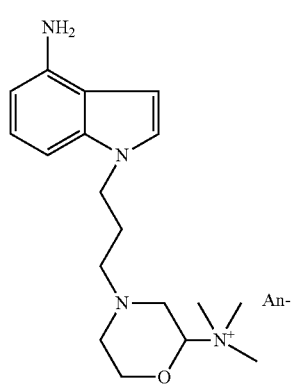

1-[3-(4-amino-1H-indol-1-yl)propyl]-N,N,N-trimethyl piperidin-3-ammonium, An- (Compound 34)

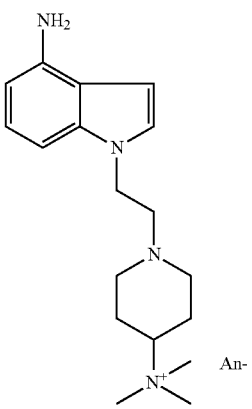

1-[2-(4-amino-1H-indol-1-yl)ethyl]-N,N,N-trimethyl piperidin-4-ammonium, An-

-continued

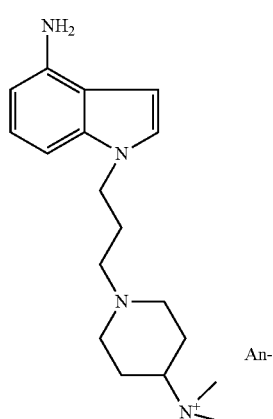

(Compound 35)

1-[3-(4-amino-1H-indol-1-yl)propyl]-N,N,N-trimethyl piperidin-4-ammonium, An−

The cationic 4-aminoindoles of general formula (I) according to the present patent application may be prepared according to various synthetic routes.

The present patent application also relates to a process for synthesizing a cationic 4-aminoindole of general formula (I) in which the radicals $R_4$ and $R_5$ represent hydrogen atoms, starting with a nitroindole of formula (II):

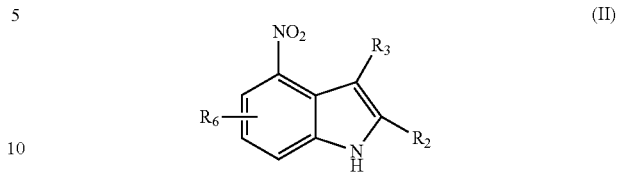

in which the definitions of the radicals $R_2$, $R_3$ and $R_6$ are as envisaged for the definition of the cationic 4-aminoindole of general formula (I), the said process comprising at least the following steps, in this order:
- alkylation of the nitroindole to substitute the nitrogen atom of the indole nucleus with a hydroxyalkyl group,
- substitution of the hydroxyl group of the hydroxyalkyl with a sulfonyl group using an alkylsulfonyl halide or a tosyl halide,
- substitution of the sulfonyl group with an aminoalkoxide or with an amine to obtain the cationic radical or a precursor of the cationic radical,
- cationization of the precursor if the product obtained in the preceding step is not cationic,
- reduction of the nitro group.

This process is summarized in the scheme below:

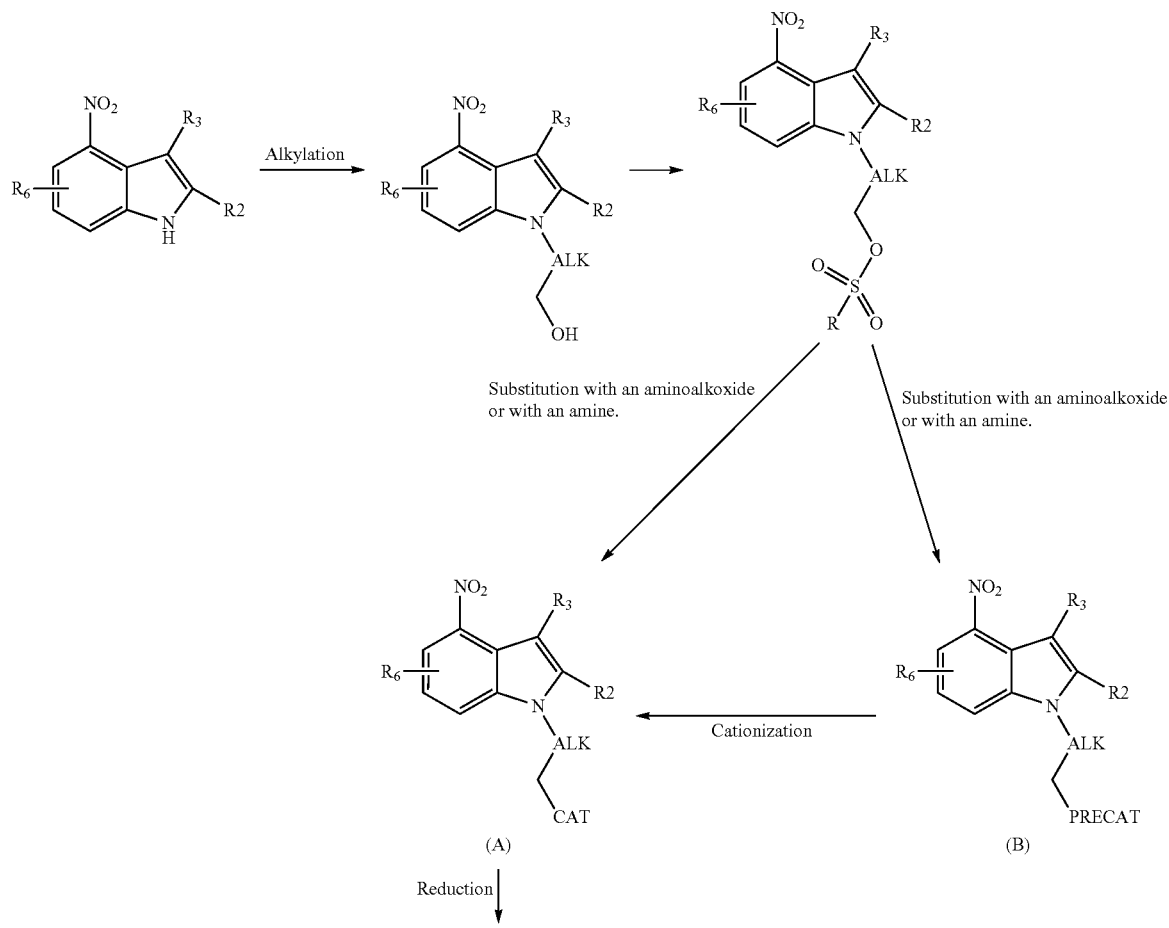

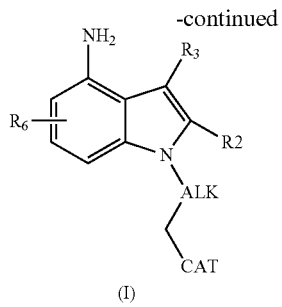

(I)

with ALK=divalent radical "corresponding" to $R_1$ without the cationic radical,
CAT=cationic radical as defined previously, the electrical neutrality being ensured by An- as defined previously,
PRECAT=radical that is cationizable into a cationic radical CAT.

The alkylation reaction is performed in a dipolar solvent such as acetone, acetonitrile, THF or in an alcohol such as ethanol, for example, in the presence of a base such as triethylamine, ethyldiisopropylamine, sodium hydroxide or potassium hydroxide, for example, with 1 to 2 equivalents of hydroxyalkyl halide for 1 to 24 hours at a temperature from 20° C. to the reflux temperature of the solvent.

The hydroxyl function thus introduced is then substituted with a halide (for example mesyl or tosyl halide) in a solvent such as acetonitrile, THF or in an alcohol such as ethanol, for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced in the preceding step is performed either by reaction with an aromatic tertiary amine such as N-methylimidazole to give the compounds (A) or by reaction with a particular primary or secondary amine, for instance N,N-dimethylethylenediamine or 2-piperidin-1-ylethanamine to give compounds (B). Alkylation of compounds (B) with at least one equivalent of alkyl halide or methyl sulfate in a solvent such as THF, acetonitrile, dioxane or ethyl acetate for 15 minutes to 24 hours at a temperature ranging from 15° C. to the reflux temperature of the solvent gives compounds (A).

The reduction of the nitro group of compounds (A) is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see Advanced Organic Chemistry, 3rd edition, J. March, 1985, Wiley Interscience, and Reduction in Organic Chemistry, M. Hudlicky, 1983, Ellis Horwood Series Chemical Science).

The present patent application also relates to the uses of a cationic 4-aminoindole of general formula (I) as a coupler for the dyeing of keratin fibres, especially human keratin fibres such as the hair.

The present patent application also relates to a cosmetic dye composition, especially for keratin fibres such as the hair, comprising, in a suitable dyeing medium, at least one cationic 4-aminoindole of general formula (I).

Preferably, the concentration of the cationic 4-aminoindole of general formula (I) is between 0.0001% and 20% and preferably between 0.005% and 6% by weight relative to the total weight of the composition.

The suitable dyeing medium generally comprises water or a mixture of water and of at least one organic solvent, for instance linear or branched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol and also aromatic alcohols, for instance benzyl alcohol or phenoxyethanol, and mixtures thereof.

Advantageously, the cosmetic composition comprises at least one cosmetic adjuvant chosen from the group formed by antioxidants, penetrants, sequestrants, fragrances, buffers, dispersants, surfactants, conditioning agents, film-forming agents, polymers, ceramides, preserving agents, nacreous agents or opacifiers, and vitamins or provitamins.

The above adjuvants are generally present in an amount for each of them of between 0.01% and 20% by weight relative to the weight of the composition.

The composition also comprises at least one oxidation base. These bases may be chosen especially from para-phenylenediamines, bis(phenyl)alkylenediamines, para-aminophenols, ortho-aminophenols and heterocyclic bases, and the addition salts thereof.

Among the para-phenylenediamines, examples that may be mentioned more particularly include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenylamino)hexan-1-ol, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, examples that may be mentioned include para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylamino-methyl)phenol, 4-amino-2-fluorophenol, 4-amino-2,6-dichlorophenol, 4-amino-6[((5'-amino-2'-hydroxy-3'-methyl)phenyl)methyl]-2-methylphenol and bis[(5'-amino-2'-hydroxy)phenyl-methane, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyridin-3-ylamine; 2-acetylaminopyrazolo-[1,5-a]-pyridin-3-ylamine; 2-morpholin-4-ylpyrazolo[1,5-a]pyridin-3-ylamine; 3-aminopyrazolo[1,5-a]pyridine-2-carboxylic acid; 2-methoxy-pyrazolo[1,5-a]pyridin-3-ylamine; (3-aminopyrazolo[1,5-a]pyridine-7-yl)methanol; 2-(3-aminopyrazolo[1,5-a]pyridine-5-yl) ethanol; 2-(3-aminopyrazolo[1,5-a]pyridin-7-yl)ethanol; (3-aminopyrazolo[1,5-a]-pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo-[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino]ethanol; 2-[(3-aminopyrazolo[1,5-a]pyridin-7-yl)-(2-hydroxyethyl)amino]ethanol; 3-aminopyrazolo[1,5-a]pyridine-5-ol; 3-amino-pyrazolo[1,5-a]pyridine-4-ol; 3-aminopyrazolo[1,5-a]pyridine-6-ol; 3-aminopyrazolo[1,5-a]pyridine-7-ol;

and also the addition salts thereof with an acid.

Among the pyrimidine derivatives, mention may be made of the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof and the tautomers thereof, when a tautomeric equilibrium exists.

Among the pyrazole derivatives that may be mentioned are the compounds described in patents DE 3 843 892, DE 4 133 957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

Generally, the concentration of the oxidation base(s) is between 0.0001% and 20% and preferably between 0.005% and 6% by weight relative to the total weight of the composition.

The composition according to the invention preferably contains at least one additional oxidation coupler, other than the cationic 4-aminoindoles of general formula (I).

Among these oxidation couplers, mention may be made especially of meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

Generally, the concentration of the oxidation coupler(s) other than the cationic 4-aminoindoles according to the present invention is between 0.0001% and 20% and preferably between 0.005% and 6% by weight relative to the total weight of the composition.

In general, the addition salts with an acid that may be used for the oxidation bases and couplers are chosen especially from the hydrochlorides, hydrobromides, sulfates, citrates, succinates, tartrates, lactates, tosylates, benzenesulfonates, phosphates and acetates.

The dye composition in accordance with the invention may also contain one or more direct dyes, which may be chosen especially from neutral, acidic or cationic nitrobenzene dyes, neutral, acidic or cationic azo direct dyes, neutral, acidic or cationic quinone and in particular anthraquinone direct dyes, azine direct dyes, methine, azomethine, triarylmethane or indoamine direct dyes and natural direct dyes. Preferably, the composition according to the invention comprises at least one dye chosen from cationic direct dyes and natural direct dyes.

Among the cationic direct dyes that may be used according to the invention, mention may be made of the cationic azo direct dyes described in patent applications WO 95/15144, WO-95/01772 and EP-714 954.

Among these compounds, mention may be made most particularly of the following dyes:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride,
- 1-methyl-4-[(methylphenylhydrazono)methyl]pyridinium methyl sulfate.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and especially henna-based poultices or extracts may also be used.

The direct dye(s) preferably represent from 0.001% to 20% by weight approximately and even more preferentially from 0.005% to 10% by weight approximately relative to the total weight of the composition.

Needless to say, a person skilled in the art will take care to select the adjuvant(s), additional oxidation dye precursors and direct dyes such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents, examples that may be mentioned include mineral or organic acids other than carboxylic acids, for instance hydrochloric acid, orthophosphoric acid, sulfuric acid, carboxylic acids such as acetic acid, tartaric acid, citric acid and lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula:

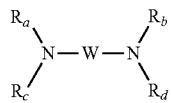

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The cosmetic composition according to the invention may be in various forms, such as in the form of liquids, creams or gels, or in any other form that is suitable for dyeing keratin fibres, and especially human hair.

The present patent application relates to a process in which the composition according to the present invention as defined previously is applied to keratin fibres for a time sufficient to develop the desired colouring in the presence of an oxidizing agent, the oxidizing agent being applied before, simultaneously with or after the composition.

The colour may be revealed at acidic, neutral or alkaline pH and the oxidizing agent may be added to the composition of the invention just before the time of use, or it may be used starting with an oxidizing composition containing it, which is applied simultaneously with or sequentially to the composition of the invention.

According to one particular embodiment, the composition according to the present invention is mixed, preferably at the time of use, with a composition containing, in a suitable dyeing medium, at least one oxidizing agent, this oxidizing agent being present in an amount sufficient to develop a coloration.

According to this particular embodiment, a ready-to-use composition is provided, which is a mixture of a composition according to the invention with at least one oxidizing agent. The mixture obtained is then applied to the keratin fibres for a time sufficient to develop the desired coloration. After a leave-on time of 3 to 50 minutes approximately and preferably 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in hair dye compositions and as defined previously.

The pH of the oxidizing composition containing the oxidizing agent is such that after mixing with the dye composition, the pH of the resulting composition applied to the keratin fibres preferably ranges between 3 and 12 approximately and even more preferentially between 5 and 11. It may be adjusted to the desired value by means of acidifying or basifying agents usually used in the dyeing of keratin fibres and as defined previously.

The ready-to-use composition that is finally applied to the keratin fibres may be in various forms, such as in the form of liquids, creams or gels, or in any other form that is suitable for dyeing keratin fibres, and especially human hair.

A subject of the present patent application is also a process for dyeing keratin fibres, in which the ready-to-use composition is applied to the said fibres for a time sufficient to develop the desired coloration.

The time sufficient to develop the desired coloration generally corresponds to a leave-on time of 3 to 50 minutes approximately and preferably 5 to 30 minutes approximately.

A subject of the invention is also a multi-compartment dyeing device or "kit" in which a first compartment contains the dye composition defined above and a second compartment contains an oxidizing agent. This device may be equipped with a means for dispensing the desired mixture on the hair, such as the devices described in patent FR-2 586 913 in the name of the Applicant.

Using this device, it is possible to dye keratin fibres by means of a process that includes the mixing of a dye composition in accordance with the invention with an oxidizing agent as defined previously, and the application of the mixture obtained onto the keratin fibres for a time sufficient to develop the desired coloration.

The examples that follow serve to illustrate the invention without, however, being limiting in nature.

EXAMPLES

Examples of Synthesis

Step 1: Synthesis of 2-(4-nitro-1H-indol-1-yl)ethanol

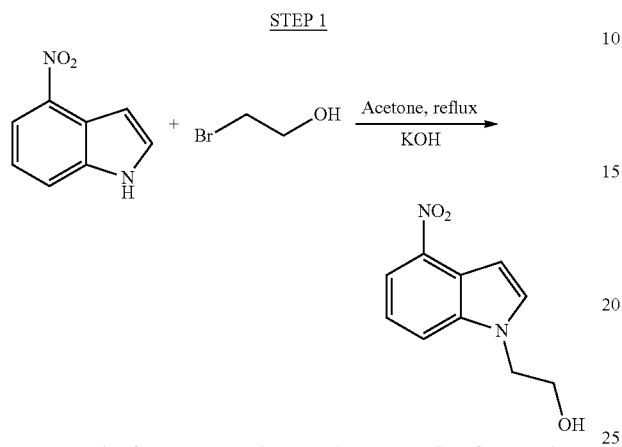

450 ml of acetone and 26 g (464 mmol) of potassium hydroxide are successively placed in a 1 liter three-necked flask equipped with a thermometer, a condenser, a bubbler, a magnetic stirrer and a dropping funnel. Once the solution has been obtained, 15 g (92.5 mmol) of 4-nitroindole are added, followed by dropwise addition of 15 ml (203.5 mmol) of 2-bromoethanol, and the mixture is refluxed for 6 hours.

The medium is cooled and the insoluble matter formed is filtered off and washed thoroughly with acetone.

The mother liquors are evaporated to dryness, the residue is then taken up in demineralized water and the pH is adjusted to neutral pH with 1N hydrochloric acid solution.

The mixture is then transferred into a separating funnel and extraction is performed using dichloromethane.

The organic phase is washed with saturated aqueous sodium chloride solution and then dried over sodium sulfate and evaporated to dryness, then purified on a column of silica using twice 15 g of crude product, to give 7.9 g of the expected compound, i.e. a synthesis yield of 41.6%.

Analysis by mass spectrometry confirms the expected compound: the quasi-molecular ions $[M^+H]^+$, $[M^+Na]^+$, $[M^+Na^+CH_3OH]^-$, $[M^-H]^-$ of the expected molecule are mainly detected.

Step 2: Synthesis of common 2-(4-nitro-1H-indol-1-yl) ethyl methanesulfonate

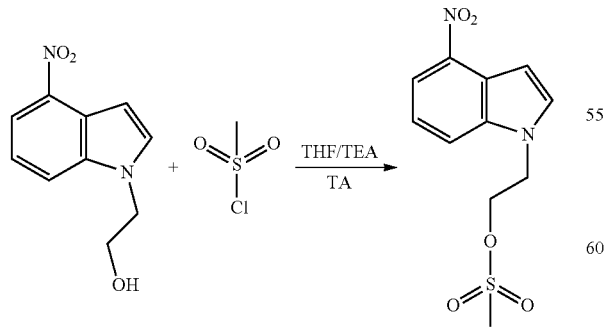

5 ml of tetrahydrofuran, 340 microliters of triethylamine and 0.5 g (2.4 mmol) of 2-(6-nitro-2,3-dihydro-1H-indol-1-yl)ethanol are successively placed in a 10 ml three-necked flask equipped with a thermometer, a condenser, a bubbler, a magnetic stirrer and an equalized-pressure dropping funnel, and after cooling to 0° C., 278 microliters (2.4 mmol) of methanesulfonyl chloride are added dropwise.

After stirring at room temperature for 6 hours, the reaction medium is poured onto 10 g of ice/water with stirring.

The yellow precipitate formed is isolated by filtration, washed thoroughly with water and then dried under vacuum in the presence of a desiccant.

560 mg (81.3% yield) of a yellow powder corresponding to the expected compound are thus obtained.

Analysis by mass spectrometry confirms the structure of the expected compound: the quasi-molecular ions [M+H]+, [M+Na]+, [M+Na+CH3OH]+, [M−H]− of the expected molecule are mainly detected.

Example 1

Synthesis of 1-[2-(4-amino-1H-indol-1-yl)ethyl]-3-methyl-1H-imidazol-3-ium methanesulfonate, methanesulfonic acid

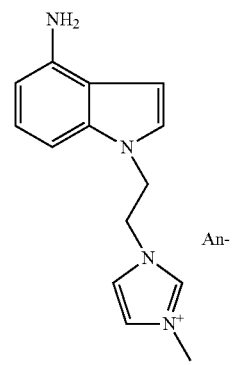 [SMILES: C[n+]1ccn(CCn2ccc3c(N)cccc32)c1]

Synthesis of 3-methyl-1-[2-(4-nitro-1H-indol-1-yl)ethyl]-1H-imidazol-3-ium methanesulfonate

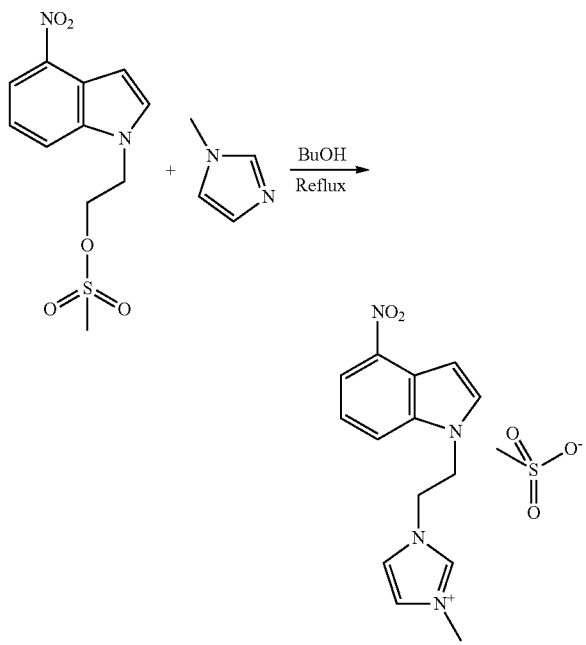

2 ml of n-butanol, 0.5 g (1.76 mmol) of 2-(4-nitro-1H-indol-1-yl)ethyl methanesulfonate and 0.28 ml (3.5 mmol) of N-methylimidazole are successively placed in a 10 ml three-necked flask equipped with a thermometer, a condenser, a bubbler and a magnetic stirrer. The reaction medium is refluxed for 2 hours.

After cooling, a yellow precipitate forms. It is filtered off by suction, and washed with n-butanol and then with diisopropyl ether.

After drying under vacuum in the presence of a desiccant, this precipitate gives 553 mg (85.9% yield) of expected compound in the form of a yellow powder.

Analysis by mass spectrometry confirms the structure of the expected compound: the expected cation is mainly detected.

Synthesis of 1-[2-(4-amino-1H-indol-1-yl)ethyl]-3-methyl-1H-imidazol-3-ium methanesulfonate, methanesulfonic acid

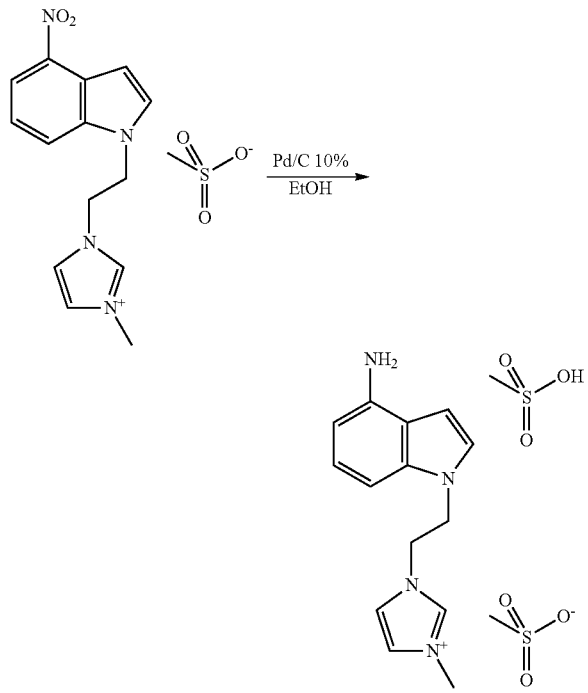

The reduction reaction by catalytic hydrogenation is performed using a hydrogenating system of H-CUBE type distributed by Serlabo, by treating a solution of 2.21 g (7.1 mmol) of 3-methyl-1-[2-(4-nitro-1H-indol-1-yl)ethyl]-1H-imidazol-3-ium methanesulfonate in a mixture of 128 ml of ethanol and 12 ml of water on a 10% Pd/C cartridge at a temperature of 80° C. and a flow rate of 1 ml per minute.

The solution containing the reduced compound is collected in an argon-saturated conical flask.

The solvent is removed on a rotavapor to give a light brown oil that crystallizes. This residue is taken up with 5 ml of methanesulfonic acid in 10 ml of ethanol and the mixture is then concentrated to dryness again.

The residue is then taken up in ethanol and crystallized very slowly by scratching.

After filtering, washing with 2-propanol and drying under vacuum in the presence of a desiccant, 2.5 g (87.5% yield) of the expected compound are obtained.

The NMR analyses ($^1$H 400 MHz and $^{13}$C 100.61 MHz DMSO-$d_6$) are in accordance with the expected structure.

Analysis by mass spectrometry confirms the structure of the expected compound: the expected cation and the fragment ion $[C_{14}H_{17}N_4]^+$ are mainly detected.

Examples of Dyeing

The following dye compositions are prepared

| Examples | 1 | 2 | 3 | 4 |
|---|---|---|---|---|
| 1-[2-(4-amino-1H-indol-1-yl)ethyl]-3-methyl-1H-imidazol-3-ium methanesulfonate, methanesulfonic acid | $10^{-3}$ mol | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — | — |
| 2-[(3-aminopyrazolo[1,5-a]pyridin-2-yl)oxy]ethanol hydrochloride | — | $10^{-3}$ mol | — | — |
| 4-(3-aminopyrazolo[1,5-a]pyridin-2-yl)-1,1-dimethylpiperazin-1-ium chloride, hydrochloride | — | — | $10^{-3}$ mol | — |
| 2-[{2-[(4-aminophenyl)amino]-ethyl}(2-hydroxyethyl)-amino]ethanol hydrochloride | — | — | — | $10^{-3}$ mol |
| Dye support (1) | (*) | (*) | (*) | (*) |
| Demineralized water qs | 100 g | 100 g | 100 g | 100 g |
| Shade observed | Nacreous blond | Blue-grey | Chromatic green | Grey-green |

(*) Dye support (1) pH 9.5:

| | |
|---|---|
| 96° ethyl alcohol | 20.8 g |
| Sodium metabisulfite as an aqueous 35% solution | 0.23 g AM |
| Pentasodium salt of diethylenetriaminepentaacetic acid as an aqueous solution at 40% by weight | 0.48 g AM |
| $C_8$-$C_{10}$ alkyl polyglucoside as an aqueous solution at 60% by weight | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% by weight of $NH_3$ | 2.94 g |

AM = Active Material

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-on time of 30 minutes, the locks are rinsed, washed with a standard shampoo, rinsed again and then dried to give the shades mentioned.

The invention claimed is:

1. Cationic 4-aminoindole of general formula (I), addition salts thereof with an acid and solvates thereof:

$$\text{(I)}$$

in which:
- $R_1$ is a linear or branched saturated $C_2$-$C_{20}$ alkyl radical, which is substituted or interrupted with a cationic radical, $R_1$ also optionally being interrupted with one or more oxygen atoms and/or with one or more groups $NR_7$;
- $R_7$ is a hydrogen atom or a linear or branched $C_1$-$C_4$ alkyl radical, a benzyl radical or an acetyl radical;
- $R_2$, $R_3$ and $R_6$, independently of each other, are chosen from: a hydrogen atom, halogens chosen from fluorine, chlorine and bromine, and linear or branched $C_1$-$C_4$ alkyl, carboxyl (—COOH) or ($C_1$-$C_4$) alkoxycarbonyl radicals;
- $R_4$ and $R_5$, independently of each other, are chosen from: a hydrogen atom and $C_1$-$C_4$ alkyl radicals;
- An- represents an anion or a mixture of anions,
- the said cationic radical being a linear, branched or cyclic, saturated or unsaturated radical, comprising a quaternary ammonium of the type —N⁻RaRb- or —N⁺RaRbRc, with Ra, Rb and Rc, which may be identical or different, representing a $C_1$-$C_6$ alkyl radical that may be substituted with a hydroxyl; or Ra and Rb together forming a saturated or unsaturated 5- to 8-membered heterocycle chosen from imidazolium, pyridinium, piperazinium, piperidinium,pyrrolidinium, morpholinium, pyrimidinium, thiazolium, benzimidazolium, benzothiazolium, oxazolium, benzotriazolium, pyrazolium, triazolium and benzoxazolium, and Rc, when it is present, being a C1-C6 alkyl radical that may be substituted with a hydroxyl.

2. Cationic 4-aminoindole according to claim 1, in which the cationic radical is chosen from trimethylammonium, triethylammonium, dimethylethylammonium, diethylmethylammonium, diisopropylmothylammonium, diethyipropylammonium, hydroxyl-ethyldiethylammonium, di-β-hydroxyethylmethylammonium, tri-β-hydroxyethylammonium, imidazolium, N-methylimidazolium, pyridinium, 1-methylpiperazin-1-ium, N,N-dimethylpiperazinium, N-methylpiperidinium, N-methylpyrrolidinium, N-methyl morpholinium, pyrimidinium, thiazolium, benzimidazolium, pyrrolidine substituted with a trimethylammonium group, piperidine substituted with a trimethylammonium group, morpholine substituted with a trimethylammonium group, trimethylethanammonium, methyldiethylmethanammonium, methyldiethylethanammonium, methylmethanopyrrolidinium and methylethanopyrrolidinium radicals.

3. Cationic 4-aminoindole according to claim 1, in which R1 is a linear or branched saturated C2-C20 alkyl radical, substituted or interrupted with a cationic radical as defined according to either of claims 1 and 2, not interrupted or interrupted with one or more oxygen atoms and/or with one or more NH groups.

4. Cationic 4-aminoindole according to claim 1, in which R1 represents a linear saturated C2-C8 alkyl radical, not interrupted or interrupted with an oxygen atom or an NH group, substituted with a cationic radical chosen from the radicals: trimethylammonium, N-methylimidazolium, N-methylpiperidinium, N,N-dimethylpiperazinium, 1-methylpiperazin-1-ium, N-methylmorpholinium, pyrrolidine substituted with a trimethylammonium group, piperidine substituted with a trimethylammonium group, morpholine substituted with a group selected from trimethylammonium, methyldiethylmethanammonium, trimethylethanammonium, methyldiethylethanammonium, methylpyrrolidiniu m, methylethanopyrrolidinium and methyl-methanopyrrolidinium.

5. Cationic 4-aminoindole according to claim 1, in which R2, R3 and R6, independently of each other, are chosen from a hydrogen atom and C1-C4 alkyl radicals.

6. Cationic 4-aminoindole according to claim 1, in which R4 and R5 are identical and represent hydrogen atoms.

7. Cationic 4-aminoindole according to claim 1, in which $R_7$ is a hydrogen atom.

8. Cationic 4-aminoindole according to claim 1, is chosen from the following compounds: 1-[2-(4-amino-1H-indol-1-yl)ethyl]-3-methyl-1H imidazol-3-ium, 2-(4-amino-1H-indol-1-yl)-N,N,N-trimethyl ethanammonium, 4-[2-(4-amino-1 H-indol-1-yl)ethyl]-1,1-dimethyl piperazin-1-ium, 2-{[2-(4-amino-1H-indol-1-yl)ethyl]amino}-N,N,N-trimethylethanammonium, 3-{[2-(4-amino-1H-indol-1-yl)ethyl]amino}-N,N,N-trimethylpropan-1-ammonium, 1-(2-{2-(4-amino-1H-indol-1-yl)ethyl]amino}ethyl)-1-methylpiperidinium, 1-3-{[2-(4-amino-1H-indol-1-yl)ethyl]amino}propyl)-1-methylpiperidinium, 1-(2-{[2-(4-amino-1H-indol-1-yl)ethyl]amino}ethyl)-1-methylpyrrolidinium, 1-(3-{[2-(4amino-1H-indol-1-yl)ethyl]amino}propyl)-1-methylpyrrolidinium, 1-(2-{[2-(4-amino-1H-indol-1-yl)ethyl]amino}ethyl)-3-methyl-1H-imidazol-3-ium, 1-(3-{[2 (4-amino-1H-indol-1-yl)ethyl]amino}propyl)-3-methyl-1H-imidazol-3-ium, 4-(2-{[2-(4-amino-1H-indol-1-yl)ethyl]amino}ethyl)-4-methylmorpholin-4-ium, 4-(3-{[2-(4-amino-1H-indol-1-yl)ethyl]amino}propyl)-4-methyl-morpholin-4-ium, 2-[2-(4-amino-1H-indol-indol-yl)ethoxy]-N,N,N-trimethylethanammonium, 1-{2-[2-(4-amino-1H-indol-1-yl)]ethoxyl-ethyl}-1-methylpyrrolidinium, 1-{2-[2-(4-amino-1H-indol-1-yl)-ethoxylethyl}-1-methylpiperidinium, 4-{2-[2-(4-amino-1H-indol-1-yl)ethoxy]ethyl}-4-methylmorphol in-4-ium, 1-{2-[2-(4-amino-1H-indol-1-yl)ethoxy]ethyl}-3-methyl-1H-imidazol-3-ium, 4-[2-(4-amino-1H-indol-1-yl)ethyl]-4-methylmorpholin-4-ium, 4-[3-(6-amino-2,3-dihydro-1H-indol-1-yl)propyl]-4-methylmorpholin-4-ium, 3-(4-amino-1H-indol-1-yl)-N,N,N-trimethylpropan-1-ammonium, 1-[3-(4-amino-1H-indol-1-yl)propyl]-3-methyl-1H-imidazol-3-ium, 4-[3-(4-amino-1H-indol-1-yl)propyl]-1,1-dimethylpiperazin-1-ium, 1-[2-(4-amino-1H-indol-1-yl)ethyl]-N,N,N-trimethylpyrrolidin-2-ammonium, 1-[3-(4-amino-1H-indol-1-yl)propyl]-N,N,N-trimethylpyrrolidin-2-ammonium, 4-{2-[3-(4-amino-1H-indol-1-yl)]ethyl }-N,N,N-trimethyl morpholin-2-ethanammonium, 4-{2-[3-(4-amino-1H-indol-1-yl)]ethyl}-N,N,N-trimethylmorpholin-2-methanammonium, 4-{2-[3-(4-amino-1H-indol-1-yl)]ethyl}-N,N,N-diethylmethylmorpholin-2-ethanammonium, 4-{2-[3-(4-amino-1H-indol-1-yl)]ethyl}-N,N,N-diethylmethylmorpholin-2-methanammonium, 4-{2-[3-(4-amino-1 H-indol-1-yl)]ethyl}-N,N,N-morpholin-2-ethan-1-methylpyrrolidinium, 4-{2-[3-(4-amino-1H-indol-1-yl)]ethyl}-N,N,N-morpholin-2-methan-1-methylpyrrolidinium, 4-{3-[3-(4-amino-1H-indol-1-yl)]propyl}-N,N,N-trimethylmorpholin-2-ethanammonium, 4-{3-[3-(4-amino-1H-indol-1-yl]propyl}-N,N,N-trimethylmorpholin-2-methanammonium, 4-{3-[3-(4-amino-1H-indol-1-yl)]propyl}-N,N,N-diethylmethylmorpholin-2-ethanammonium, 4-{3-[3(4-amino-1H-indol-1-yl)]propyl}-N,N,N-diethylmethyl-morpholin-2-methanammonium, 4-{3-[3-(4-amino-1H-indol-1-yl)1-propyl}-N,N,N-morpholin-2-ethan-1-methylpyrrolidinium, 4-{3-[3-(4-amino-1H-indol-1-yl)]propyl}-N,N,N-morpholin-2-methan-1-methyl pyrrolidinium, 1-[2-(4-amino-1H-indol-1-yl)ethyl]-N,N,N-trimethyl-piperidin-3-ammonium, 1-[3-(4-amino-1 H-indol-1-yl)propyl]-N,N,N-trimethylpiperidin-3-ammonium, 1-[2-(4-amino-1H-indol-1-yl)ethyl]-N,N,N-trimethylpiperidin-4-ammonium, 1-[3-(4-amino-1H-indol-1-yl)-propyl]-N,N,N-trimethylpiperidin-4-ammonium.

9. Process for synthesizing a cationic 4-aminoindole of general formula (I) as defined in claim 6, starting with an indole of formula (II):

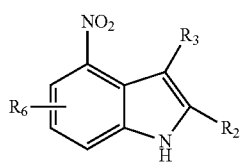

in which the radicals R2, R3, and R6 independently from each other, are chosen from: a hydrogen atom, halogens chosen from fluorine, chlorine and bromine, and linear or branched C1-C4 alkyl, carboxyl (—COOH) or (C1-C4)alkoxycarbonyl radicals, the said process comprising at least the following steps, in this order:
   alkylation of the nitroindole to substitute the nitrogen atom of the indole nucleus with a hydroxyalkyl group,
   substitution of the hydroxyl group of the hydroxyalkyl with a sulfonyl group using an alkylsulfonyl halide or a tosyl halide,
   substitution of the sulfonyl group with an aminoalkoxide to obtain the cationic radical or with an amine to obtain a precursor of the cationic radical,
   if the substitution was performed with an amine, cationization of the precursor,
   reduction of the nitro group.

10. A coupler for dyeing human keratin fibers, especially hair, comprising the cationic 4-aminoindole of a formula (I) as defined in claim 1.

11. Cosmetic dye composition comprising, in a suitable dyeing medium, at least one cationic 4-aminoindole of formula (I) as defined in claim 1.

12. Composition according to claim 11, characterized in that it is a ready-to-use composition comprising at least one oxidizing agent chosen from hydrogen peroxide, urea peroxide, alkali metal bromates, persalts, peracids and oxidase enzymes.

13. Process for dyeing keratin fibres, characterized in that the composition according to claim 11 is applied to the said fibers, for a time sufficient to develop the desired coloration in the presence of an oxidizing agent, the oxidizing agent being applied before, simultaneously with or after the composition.

14. Multi-compartment device, a first compartment containing the cosmetic composition for dyeing keratin fibers as defined in claim 11, and a second compartment containing an oxidizing agent.

* * * * *